US012731388B2

(12) United States Patent
Fang et al.

(10) Patent No.: US 12,731,388 B2
(45) Date of Patent: Sep. 8, 2026

(54) MACHINE LEARNING SYSTEM AND METHOD FOR PREDICTING ALZHEIMER'S DISEASE BASED ON RETINAL FUNDUS IMAGES

(71) Applicant: UNIVERSITY OF FLORIDA RESEARCH FOUNDATION, Gainesville, FL (US)

(72) Inventors: Ruogu Fang, Gainesville, FL (US); Jianqiao Tian, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 192 days.

(21) Appl. No.: 17/928,345

(22) PCT Filed: May 28, 2021

(86) PCT No.: PCT/US2021/034916
§ 371 (c)(1),
(2) Date: Nov. 29, 2022

(87) PCT Pub. No.: WO2021/243246
PCT Pub. Date: Dec. 2, 2021

(65) Prior Publication Data

US 2023/0245772 A1 Aug. 3, 2023

Related U.S. Application Data

(60) Provisional application No. 63/032,018, filed on May 29, 2020.

(51) Int. Cl.
*G06V 10/82* (2022.01)
*G16H 50/20* (2018.01)

(52) U.S. Cl.
CPC ............. *G06V 10/82* (2022.01); *G16H 50/20* (2018.01)

(58) Field of Classification Search
CPC ...................................................... G16H 50/20
(Continued)

(56) References Cited

U.S. PATENT DOCUMENTS 8,885,901 B1 11/2014 Solanki et al.
9,521,975 B2 12/2016 Verdooner et al.
(Continued)

OTHER PUBLICATIONS

Turbert, David, Fundus, American Academy of Opthalmology, dated Jan. 14, 2020, downloaded from https://www.aao.org/eye-health/anatomy/fundus on Nov. 12, 2024 (Year: 2020).*
(Continued)

*Primary Examiner* — Scott D Gartland
(74) *Attorney, Agent, or Firm* — Thomas | Horstemeyer, LLP

(57) ABSTRACT

A machine learning system and method are disclosed that enable full automation of the process of analyzing retinal fundus images to predict Alzheimer's disease, thereby obviating the need for manual labeling of retinal features while also improving prediction accuracy. A machine learning system and method are disclosed that classify retinal features and predict, based on the classified retinal features, the onset or presence of Alzheimer's disease in a human subject. The system comprises a processor configured to perform one or more machine learning models and a memory device in communication with the processor. The machine learning model(s) is trained to process retinal fundus images acquired by an image acquisition system to classify retinal features contained in the images and to predict, based on the classified retinal features, whether the images are indicative of the presence or onset of Alzheimer's disease.

14 Claims, 11 Drawing Sheets

(58) Field of Classification Search
USPC .............................................................. 705/2
See application file for complete search history.

(56) References Cited

U.S. PATENT DOCUMENTS

| | | | | |
|---|---|---|---|---|
| 2014/0348750 | A1 * | 11/2014 | Vince ........................ | G01J 3/00<br>514/17.7 |
| 2016/0092721 | A1 * | 3/2016 | Kanagasingam .... | G06V 40/193<br>348/78 |
| 2019/0042828 | A1 * | 2/2019 | Solanki ............... | G06F 16/5866 |
| 2022/0157470 | A1 * | 5/2022 | Sylvestre ............... | G16H 10/20 |

OTHER PUBLICATIONS

What are support vector machines (SVMs)?, IBM, dated Dec. 27, 2023, downloaded from https://www.ibm.com/topics/support-vector-machine on Nov. 13, 2024 (Year: 2023).*

Berisha et al., Retinal abnormalities in early Alzheimer's disease. Invest Ophthalmol Vis Sci. May 2007;48(5):2285-9. doi: 10.1167/iovs.06-1029. PMID: 17460292. Downloaded via https://pubmed.ncbi.nlm.nih.gov/17460292/ and https://iovs.arvojournals.org/article.aspx?articleid=2164340 (Year: 2007).*

Vlachos et al., Multi-scale retinal vessel segmentation using line tracking, Computerized Medical Imaging and Graphics, vol. 34, Issue 3, 2010, pp. 213-227, ISSN 0895-6111, https://doi.org/10.1016/j.compmedimag.2009.09.006. Downloaded Mar. 21, 2026 (Year: 2010).*

Csincsik et al., Peripheral Retinal Imaging Biomarkers for Alzheimer's Disease: A Pilot Study. Ophthalmic Res. 2018;59(4):182-192. doi: 10.1159/000487053. Epub Apr. 5, 2018. PMID: 29621759; PMCID: PMC5985743. Downloaded Mar. 21, 2026 from https://pmc.ncbi.nlm.nih.gov/articles/PMC5985743/ (Year: 2018).*

International search report for PCT/US2021/034916 mailed May 28, 2021.

DeBuc, et al., "Identification of Retinal Biomarkers in Alzheimer's Disease Using Optical Coherence Tomography, Recent Insights, Challenges, and Opportunities", J. Clin Med. Jul. 2019 8(7).

* cited by examiner

Table 1: Cohort Characteristics of All Extracted Groups

| | Number of Subjects (Male/Female) | Number of Images (Left Eye/Right Eye) | Age at Recruitment (Mean/Std.) |
|---|---|---|---|
| AD Dementia Group | 87 (46/41) | 122 (77/45) | 65.17 (4.16) |
| Five Control Groups | 87 (46/41) | 122 (77/45) | 65.17 (4.16) |

FIG. 5

Table 2: Performance comparison of the overall classification for AD vs. normal controls (NC)* *without* feature selection

| Classification Groups | Accuracy (Mean/std) | Precision(PPV) (Mean/std) | NPV (Mean/std) | Specificity (TNR) (Mean/std) | Sensitivity (TPR) (Mean/std) | F1-Score (Mean/std) |
|---|---|---|---|---|---|---|
| AD group vs. 1st normal control group | **0.734 (0.062)** | **0.778 (0.048)** | **0.694 (0.077)** | **0.808 (0.069)** | 0.648 (0.110) | **0.702 (0.078)** |
| AD group vs. 2nd normal control group | *0.674 (0.072)* | 0.692 (0.084) | *0.658 (0.064)* | 0.758 (0.085) | *0.584 (0.143)* | *0.632 (0.095)* |
| AD group vs. 3rd normal control group | 0.680 (0.090) | 0.684 (0.091) | 0.674 (0.077) | *0.678 (0.118)* | **0.678 (0.081)** | 0.680 (0.073) |
| AD group vs. 4th normal control group | 0.668 (0.074) | 0.666 (0.078) | 0.664 (0.084) | 0.706 (0.079) | 0.624 (0.087) | 0.644 (0.073) |
| AD group vs. 5th normal control group | *0.654 (0.085)* | *0.658 (0.078)* | 0.664 (0.088) | 0.686 (0.074) | 0.618 (0.176) | 0.630 (0.130) |
| Average over five datasets | 0.682 | 0.6956 | 0.6708 | 0.7272 | 0.6304 | 0.6576 |

Note: * The mean and standard deviation values were extracted from five-fold cross validations.

Bold font represents the most optimal performance for each measurement among five-fold cross validations. *Italic* font represents the least optimal performance.

Abbreviation: AD= dementia caused by Alzheimer's disease, NC= normal control, PPV= positive predictive value, NPV= negative predictive value, TNR= true negative rate, TPR= true positive rate.

FIG. 7

Table 3: Performance comparison of the overall classification for AD vs. normal controls (NC)* *with* feature selection

| Classification Groups | Accuracy (Mean/std) | Precision(PPV) (Mean/std) | NPV (Mean/std) | Specificity (TNR) (Mean/std) | Sensitivity (TPR) (Mean/std) | F1-Score (Mean/std) |
|---|---|---|---|---|---|---|
| AD group vs. 1st normal control group | 0.8216 (0.0136) | 0.8504 (0.0186) | 0.7977 (0.0144) | 0.8623 (0.0200) | 0.7811 (0.0189) | 0.8142 (0.0143) |
| AD group vs. 2nd normal control group | 0.8280 (0.0142) | 0.8316 (0.0115) | 0.7883 (0.0191) | 0.8434 (0.0119) | 0.7730 (0.0256) | 0.8010 (0.0167) |
| AD group vs. 3rd normal control group | 0.8300 (0.0110) | **0.8561 (0.0121)** | 0.8079 (0.0177) | **0.8664 (0.0145)** | 0.7934 (0.0250) | 0.8233 (0.0134) |
| AD group vs. 4th normal control group | **0.8426 (0.0129)** | 0.8432 (0.0105) | **0.8423 (0.0170)** | 0.8434 (0.0105) | **0.8418 (0.0193)** | **0.8424 (0.0137)** |
| AD group vs. 5th normal control group | *0.7999 (0.0130)* | *0.8172 (0.0100)* | *0.7831 (0.0197)* | *0.8270 (0.0119)* | *0.7730 (0.0276)* | *0.7942 (0.0161)* |
| Average over five datasets | 0.82442 | 0.8397 | 0.80436 | 0.8483 | 0.79346 | 0.81502 |

Note: * The mean and standard deviation values were extracted from five-fold cross validations.

Bold font represents the most optimal performance for each measurement among five-fold cross validations. *Italic* font represents the least optimal performance.

Abbreviation: AD= dementia caused by Alzheimer's disease, NC= normal control, PPV= positive predictive value, NPV= negative predictive value, TNR= true negative rate, TPR= true positive rate.

MACHINE LEARNING SYSTEM AND METHOD FOR PREDICTING ALZHEIMER'S DISEASE BASED ON RETINAL FUNDUS IMAGES

CROSS REFERENCE TO RELATED APPLICATIONS

This application is the 35 U.S.C. § 371 national stage application of PCT Application No. PCT/US2021/034916, filed May 28, 2021, which claims priority to, and the benefit of, U.S. Provisional Application No. 63/032,018, filed on May 29, 2020, entitled "A Machine Learning System And Method For Predicting Alzheimer's Disease Based On Retinal Fundus Images," both of which are hereby incorporated by reference herein in their entireties.

TECHNICAL FIELD

The present disclosure is directed to a machine learning system and method for predicting Alzheimer's disease based on retinal fundus images.

BACKGROUND

Alzheimer's disease is the leading neurodegenerative disease, estimated to affect roughly 13-16 million patients by 2050. Similar to other neurodegenerative diseases, neural damage caused by Alzheimer's disease is often irreversible. Current clinical treatment strategies focus on slowing down the accumulation of pathology, not restoration of neurological function. Therefore, routine screening and early diagnosis are critical in maximizing treatment benefits and preserving neural functions.

The current gold standard for diagnosing Alzheimer's disease is based on detecting amyloid-beta abnormality. This diagnosing evaluation can be done cerebrospinal fluid (CSF), but this invasive process introduces health risks to patients. Non-invasive brain imaging, such as positron emission tomography (PET) combined with structural MRI imaging, has been evaluated as an alternative to CSF for accurate and sensitive diagnosis of Alzheimer's disease. These techniques can capture multiple characteristics of the brain, such as the structural changes in the brain, amyloid-beta density, or neural tissue metabolism activity. Nevertheless, these neuroimaging modalities still cannot fulfill the demand for timely Alzheimer's disease screening because they are relatively expensive and have limited accessibility. Amyloid PET typically costs three thousand to four thousand US dollars out of patients' pockets.

Alternatively, the retina presents a readily accessible window for extracting potential biomarkers of Alzheimer's disease. The retina is the only component of the nervous system that can be directly observed in vivo. Recent studies demonstrate that retinal fundus images display pathological features associated with the early stage of neurodegeneration diseases. For example, the thickness of the retinal nerve fiber layer and visual acuity are associated with early-stage cognitive impairment. In pre-symptomatic transgenic Alzheimer's disease mice, amyloid-beta plaques have been observed to emerge 2.5 months earlier on the retina than in the brain.

Among these retinal biomarkers, retinal vasculature frequently has a marked association with Alzheimer's disease. Abnormal narrowing in retinal venous blood column diameter and decrease blood flows are reported to be correlated in patients with Alzheimer's disease, potentially explaining the observed reduced retinal oxygen metabolism rate in mild cognitive impairment subjects group. A sparse fundus vascular network with decreased vascular fractal dimensions has a strong association with dementia. The retinal neurovascular coupling is also found to be impaired in subjects with Alzheimer's disease compared to healthy aging. The emerging evidence drives one to assume that retinal vasculature could potentially be useful for early detection of Alzheimer's disease. However, previous retinal imaging studies are limited by two common drawbacks. First, they involve a relatively high level of manual labeling, such as segmenting and measuring the thickness of the retinal nerve fiber layer. This manual labeling requirement potentially introduces human error. Second, the investigated features were generated based on fixed hand-picked rules and contained less adaptability.

Recent studies of automated machine learning applied to retinal fundus images have shown promising results in detecting several diseases, including glaucoma, diabetic retinopathy, anemia, choroidal neovascularization, central serous chorioretinopathy, vitreomacular traction syndrome, as well as identifying cardiovascular risk factors such as gender, smoking status, systolic blood pressure, and body mass index.

A need exists for a machine learning system and method that fully automate the process of analyzing retinal fundus images to predict Alzheimer's disease, thereby obviating the need for manual labeling of retinal features while also improving prediction accuracy.

SUMMARY

A machine learning system and method are disclosed herein that can fully automate the process of analyzing retinal fundus images to predict Alzheimer's disease, thereby obviating the need for manual labeling of retinal features while also improving prediction accuracy. The machine learning method and system disclosed herein classify retinal features and predict, based on the classified retinal features, the onset or presence of Alzheimer's disease in a human subject. The system comprises a processor configured to perform at least one trained machine learning model and a memory device. The trained machine learning model has been trained on stored retinal fundus images obtained from at least a first group of human subjects who have previously been diagnosed as having Alzheimer's disease and at least a first group of human subjects who have not previously been diagnosed as having Alzheimer's disease. The trained machine learning model performs a process comprising:

receiving a retinal fundus image that has been acquired by an image acquisition system;

processing the acquired retinal fundus image to classify one or more retinal features contained in the acquired retinal fundus image; and predicting, based on the classification, whether the retinal fundus image is indicative of an onset or presence of Alzheimer's disease in the human subject.

In accordance with a representative embodiment of the machine learning system, the trained machine learning model is implemented in computer instructions stored in the memory device for execution by the processor.

In accordance with a representative embodiment of the machine learning system, the trained machine learning model is configured in a multiple-stage (multi-stage) pipeline architecture comprising multiple stages that are separately trained.

In accordance with a representative embodiment of the machine learning system, the multi-stage pipeline architecture comprises at least first, second and third stages comprising, respectively, a trained image quality selector machine learning model, a trained vessel map generator machine learning model, and a trained Alzheimer disease classifier machine learning model, the second stage following the first stage and the third stage following the second stage.

In accordance with a representative embodiment of the machine learning system, the trained image quality selector machine learning model is used during training of the Alzheimer disease classifier machine learning model to classify retinal fundus images inputted to the first stage as being either of sufficient image quality or insufficient image quality and to output retinal fundus images classified as being of sufficient image quality to the second stage. During training of the Alzheimer disease classifier machine learning model, the trained vessel map generator machine learning model generates respective vessel maps for each respective retinal fundus image inputted to the second stage and outputs the vessel maps to the third stage. During training of the Alzheimer's disease classifier machine learning model, the vessel maps outputted to the third stage are used to train the Alzheimer's disease classifier model.

In accordance with a representative embodiment of the machine learning system, after the Alzheimer disease classifier machine learning model has been trained to classify retinal fundus images as being from a human subject having Alzheimer's disease, a retinal fundus image obtained from a patient is processed by the trained vessel map generator machine learning model to produce a respective vessel map that is outputted to the third stage. The respective vessel map is processed by the trained Alzheimer's disease classifier machine learning model to predict, based on the classification, whether the retinal fundus image is indicative of an onset or presence of Alzheimer's disease in the human subject.

In accordance with a representative embodiment of the machine learning system, a saliency map generator in the third stage generates respective saliency maps from the respective vessel maps generated by the trained vessel map generator learning machine model.

In accordance with a representative embodiment of the machine learning system, the trained image quality selector machine learning model comprises multiple trained image quality selector machine learning models arranged in a pipeline, and a retinal fundus image is only outputted to the second stage if all of the trained image quality selector machine learning models classified the retinal fundus image as being of sufficient image quality.

The machine learning method comprises:

in a processor configured to perform at least one trained machine learning model:

- receiving a retinal fundus image that has been acquired by an image acquisition system;
- processing the acquired retinal fundus image to classify one or more retinal features contained in the acquired retinal fundus image; and
- predicting, based on the classification, whether the retinal fundus image is indicative of an onset or presence of Alzheimer's disease in the human subject;

The trained machine learning model used in the method has been trained on stored retinal fundus images obtained from at least a first group of human subjects who have previously been diagnosed as having Alzheimer's disease and at least a first group of human subjects who have not previously been diagnosed as having Alzheimer's disease.

In accordance with a representative embodiment of the machine learning method, the trained machine learning model is configured in a multiple-stage (multi-stage) pipeline architecture comprising multiple stages that are separately trained.

In accordance with a representative embodiment of the machine learning method, the multi-stage pipeline architecture comprises at least first, second and third stages comprising, respectively, a trained image quality selector machine learning model, a trained vessel map generator machine learning model, and a trained Alzheimer disease classifier machine learning model, the second stage following the first stage and the third stage following the second stage.

In accordance with a representative embodiment of the machine learning method, the trained image quality selector machine learning model is used during training of the Alzheimer disease classifier machine learning model to classify retinal fundus images inputted to the first stage as being either of sufficient image quality or insufficient image quality and to output retinal fundus images classified as being of sufficient image quality to the second stage. During training of the Alzheimer disease classifier machine learning model, the trained vessel map generator machine learning model generates respective vessel maps for each respective retinal fundus image inputted to the second stage and outputs the vessel maps to the third stage. During training of the Alzheimer's disease classifier machine learning model, the vessel maps outputted to the third stage are used to train the Alzheimer's disease classifier model.

In accordance with a representative embodiment of the machine learning method, after the Alzheimer disease classifier machine learning model has been trained to classify retinal fundus images as being from a human subject having Alzheimer's disease, a retinal fundus image obtained from a patient is processed during the processing step by the trained vessel map generator machine learning model to produce a respective vessel map that is outputted to the third stage. The respective vessel map is processed by the trained Alzheimer's disease classifier machine learning model during the predicting step to predict, based on the classification, whether the retinal fundus image is indicative of an onset or presence of Alzheimer's disease in the human subject.

In accordance with a representative embodiment of the machine learning method, the trained Alzheimer's disease classifier machine learning model further comprises a saliency map generator for generating respective saliency maps from the respective vessel maps generated by the trained vessel map generator learning machine model.

The machine learning model can comprise computer instructions for execution by a processor, in which case the machine learning model can be embodied on a non-transitory computer-readable medium comprising:

- a first computer code portion for receiving a retinal fundus image that has been acquired by an image acquisition system;
- a second computer code portion that processes the acquired retinal fundus image to classify one or more retinal features contained in the acquired retinal fundus image; and
- a third computer code portion that predicts, based on the classification, whether the retinal fundus image is indicative of an onset or presence of Alzheimer's disease in the human subject;

In accordance with a representative embodiment of the machine learning model, it is configured in a multiple-stage (multi-stage) pipeline architecture comprising multiple stages that are separately trained.

In accordance with a representative embodiment of the machine learning model, the multi-stage pipeline architecture comprises at least first, second and third stages comprising, respectively, a trained image quality selector machine learning model, a trained vessel map generator machine learning model, and a trained Alzheimer disease classifier machine learning model, the second stage following the first stage and the third stage following the second stage.

In accordance with a representative embodiment of the machine learning model, the trained image quality selector machine learning model is used during training of the Alzheimer disease classifier machine learning model to classify retinal fundus images inputted to the first stage as being either of sufficient image quality or insufficient image quality and outputting retinal fundus images classified as being of sufficient image quality to the second stage. During training of the Alzheimer disease classifier machine learning model, the trained vessel map generator machine learning model generates respective vessel maps for each respective retinal fundus image inputted to the second stage and outputs the vessel maps to the third stage. During training of the Alzheimer's disease classifier machine learning model, the vessel maps outputted to the third stage are used to train the Alzheimer's disease classifier model.

In accordance with a representative embodiment of the machine learning model, after the Alzheimer disease classifier machine learning model has been trained to classify retinal fundus images as being from a human subject having Alzheimer's disease, a retinal fundus image obtained from a patient is processed by the trained vessel map generator machine learning model to produce a respective vessel map that is outputted to the third stage. The respective vessel map is processed by the trained Alzheimer's disease classifier machine learning model to predict, based on the classification, whether the retinal fundus image is indicative of an onset or presence of Alzheimer's disease in the human subject.

In accordance with a representative embodiment of the machine learning method, the Alzheimer disease classifier machine learning model comprises a saliency map generator in the third stage for generating respective saliency maps from the respective vessel maps generated by the trained vessel map generator learning machine model.

These and other features and advantages will become apparent from the following description, drawings and claims.

BRIEF DESCRIPTION OF THE DRAWINGS

FIG. 5 shows a table of cohort characteristics of Alzheimer's disease (AD) group subjects and healthy control group subjects that were used to train and verify the accuracy of the system shown in FIG. 1.

FIG. 6A shows that for each AD group subject, the matched healthy control group subject was selected with the identical combination of gender and age; FIG. 6B shows that, as a result of selecting the healthy control group subjects in this manner depicted in FIG. 6A, the healthy control group subjects and AD group subjects have identical distributions of gender and age.

FIG. 7 shows a table of performance comparison of overall classification results achieved by the machine learning system shown in FIG. 1 for five classification groups of AD group subjects vs healthy control group subjects without feature selection being used by the system.

FIG. 8 shows a table of performance comparison of overall classification results achieved by the machine learning system shown in FIG. 1 for five classification groups of AD group subjects vs healthy control group subjects with feature selection being used by the system.

DETAILED DESCRIPTION

Figure 1:
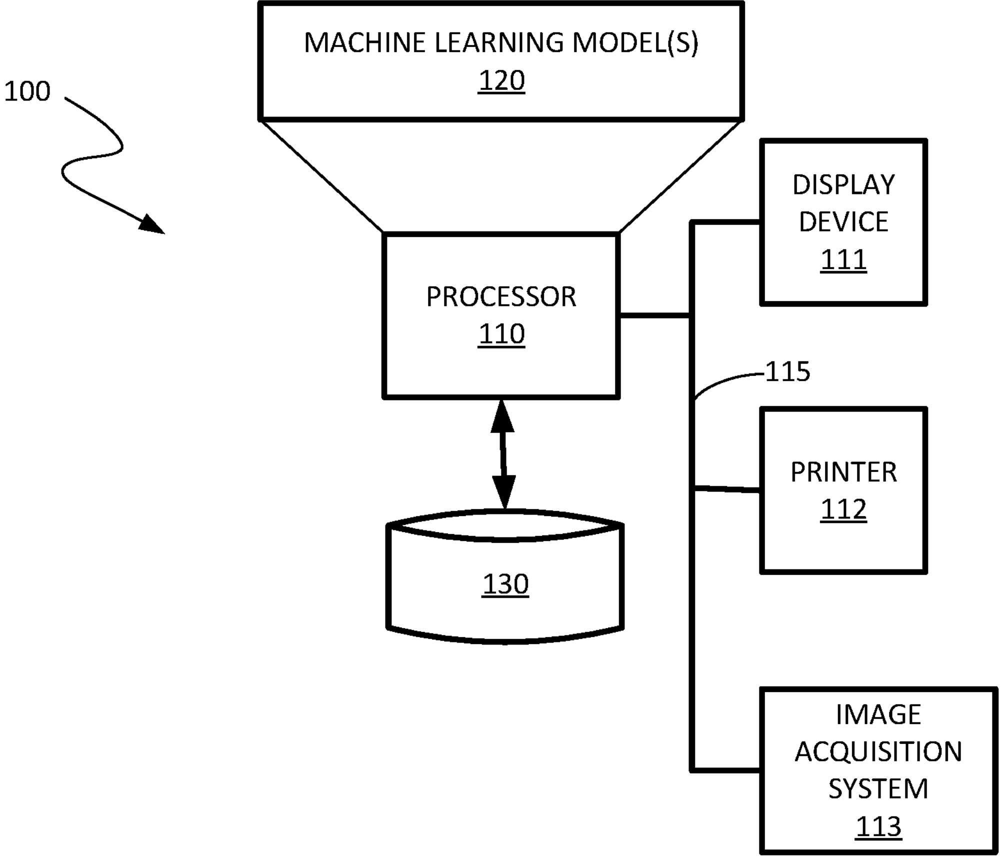
FIG. 1 is a block diagram of the machine learning system 100 in accordance with a representative embodiment for predicting Alzheimer's disease in a human subject.

A machine learning system and method are disclosed herein that enable full automation of the process of analyzing retinal fundus images to predict Alzheimer's disease, thereby obviating the need for manual labeling of retinal features while also improving prediction accuracy. The machine learning method and system classify retinal features and predict, based on the classified retinal features, the onset or presence of Alzheimer's disease in a human subject. The system comprises a processor configured to perform at least one machine learning model and a memory device in communication with the processor. The machine learning model(s) is trained to process retinal fundus images acquired by an image acquisition system to classify retinal features contained in the images and to predict, based on the classified retinal features, whether the images are indicative of the presence or onset of Alzheimer's disease.

In the following detailed description, for purposes of explanation and not limitation, exemplary, or representative, embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments, Such methods and apparatuses are clearly within the scope of the present teachings.

The terminology used herein is for purposes of escribing particular embodiments only and is not intended to be limiting. The defined terms are in addition to the technical and scientific meanings of the defined terms as commonly understood and accepted in the technical field of the present teachings.

As used in the specification and appended claims, the terms “a,” “an,” and “the” include both singular and plural referents, unless the context clearly dictates otherwise. Thus, for example, “a device” includes one device and plural devices.

Relative terms may be used to describe the various elements’ relationships to one another, as illustrated in the accompanying drawings. These relative terms are intended to encompass different orientations of the device and/or elements in addition to the orientation depicted in the drawings.

It will be understood that when an element is referred to as being “connected to” or “coupled to” or “electrically coupled to” another element, it can be directly connected or coupled, or intervening elements may be present.

The term “memory” or “memory device”, as those terms are used herein, are intended to denote a non-transitory computer-readable storage medium that is capable of storing computer instructions, or computer code, for execution by one or more processors. References herein to “memory” or “memory device” should be interpreted as one or more memories or memory devices. The memory may, for example, be multiple memories within the same computer system. The memory may also be multiple memories distributed amongst multiple computer systems or computing devices.

A “processor”, as that term is used herein encompasses an electronic component that is configured to perform operations in software, firmware, hardware or a combination thereof. For example, a processor may an electronic component that executes a computer program or executable computer instructions. As another example, a processor may be an electronic component that performs operations in hardware, such as in combinational logic of a state machine, for example, or in a combination of hardware and firmware or software, such as an application specific integrated circuit (ASIC) in which logic gates may be configured by firmware that can be periodically updated to reconfigure the logic gates. References herein to a computer comprising “a processor” should be interpreted as one or more processors or processing cores. The processor may, for instance, a multi-core processor. A processor may also refer to a collection of processors within a single computer system or distributed amongst multiple computer systems. The term “computer” should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

FIG. 1 is a block diagram of the machine learning system 100 in accordance with a representative embodiment for predicting Alzheimer’s disease in a human subject. A processor 110 of the system 100 is configured to perform one or more machine learning models 120, which can be implemented in hardware, software, firmware, or a combination thereof. A non-transitory computer-readable memory device 130 of the system 100 can be used to store any computer instructions comprising the model(s) 120. The memory device 130 also typically stores a database of retinal fundus images that are used by the machine learning model(s) 120, as described below in detail, although the database could be at some other location that is external to the system 100 and accessible by the processor 110 via a network.

The system 100 may optionally include a display device 111, a printer 112 and an image acquisition system 113. In some embodiments of the system 100, the image acquisition system 113 acquires fundus images for processing by the machine learning model(s) 120. In other embodiments of the system 100, the fundus images are provided to the system 100. Therefore, the image acquisition system 113 can be part of the system 100 or external to the system 100. The components 110, 111, 112, 113 and 130 of the system 100 are in communication with one another over one or more networks or buses represented generally by reference number 115. The components 110, 111, 112, 113 and 130 can be co-located or they can be distributed over one or more networks.

The machine learning model(s) 120 is trained to classify retinal features contained in retinal fundus images and to predict, based on the classification, the onset or presence of Alzheimer’s disease in a human subject. The manner in which training is performed and the manner in which the system 100 is used to predict the onset or presence of Alzheimer’s disease in a human subject are described below in detail with reference to FIGS. 2-10. Once trained, the machine learning model(s) 120 analyzes retinal fundus images captured by the image acquisition system 113 to identify and classify retinal features contained in the images. Based on the classification of the retinal features, the machine learning model(s) 120 predicts the onset or presence of Alzheimer’s disease in a human subject.

In the following, a discussion is provided of a representative embodiment of the system 100 and of the experiments that were performed using it. It should be noted that the inventive principles and concepts disclosed herein are not limited to this embodiment of the system or of the processes that were performed using it.

For this representative embodiment, a recently released open-access database called the UK Biobank was used to train and test the machine learning system 100. It should be noted, however, that the inventive principles and concepts are not limited with respect to the database that is used to train the system 100. The UK Biobank is a prospective, ongoing nation-wide cohort following ~500,000 individuals with ages ranging from 40 to 69 (at the time of initial enrollment) across the United Kingdom. This unprecedent database has 7,562 fields including imaging, genetics, clinical, and environmental exposure data. The rich retinal imaging and diagnosis data in UK Biobank enables retinal biomarkers for Alzheimer’s disease to be studied through automated machine learning.

The UK Biobank provides an opportunity to develop and validate the method disclosed herein for Alzheimer’s disease detection from the general population, in contrast to existing research built on cohorts of patients with specific diseases. The quality of image data from the UK Biobank is also more consistent with clinical data collected in everyday healthcare practice, compared to high-quality research-oriented data collected in existing studies. For example, the retinal fundus images in the UK Biobank were collected as a viewfinder for follow-up optical coherence tomography (OCT), resulting in fundus images with substantial varying quality. The inventors chose to evaluate the performance of the machine learning methodology disclosed herein on a real-world clinically-collected database rather than high-quality research-oriented databases, since one of the objectives was to estimate how much of an impact the method disclosed herein could bring to the clinical community.

Another advantage of using the UK Biobank to address this research question is the quality of dementia labels. The study disclosed herein the "Dementia Outcome: Alzheimer's disease" label from UK Biobank Electronic Health Records data to identify subjects with definite Alzheimer's Disease Diagnosis, which is based on a comprehensive evaluation procedure instead of a single test-based label, making this AD diagnosis more reliable. In sum, the UK Biobank enables the development of an automated machine learning method to classify Alzheimer's disease dementia, distinct from healthy aging, by identifying retinal changes associated with Alzheimer's disease using clinical-level data collected from the general population. In other words, the methods presented herein are immediately and highly generalizable.

Figure 2:
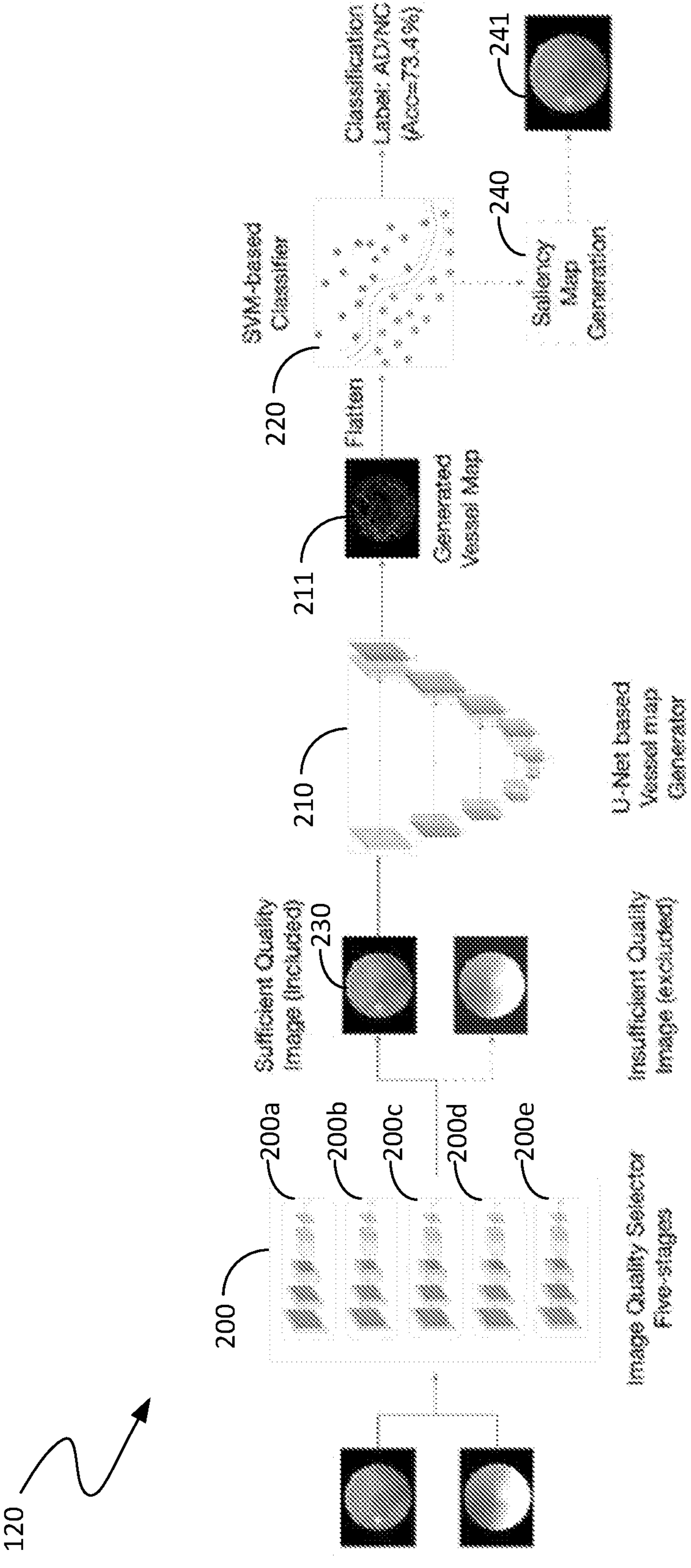
FIG. 2 is a block diagram of an overall pipeline architecture of a machine learning model(s) of the system shown in FIG. 1 in accordance with a representative embodiment.

FIG. 2 is a block diagram of an overall pipeline architecture of the machine learning model(s) 120 in accordance with a representative embodiment. In accordance with this embodiment, the pipeline architecture comprises three major machine learning stages, namely, an image quality selection stage 200, a vessel map segmentation stage 210, and an SVM-based classifier stage 220. Compared to typical end-to-end architectures of machine learning systems, this multi-stage pipeline architecture has an advantage of being modular, which allows each stage to be trained independently. Consequently, if the trained pipeline is transferred to a new database, only part of the pipeline needs to be trained, with easier-to-obtain labels.

In accordance with this representative embodiment, the pipeline is a multi-stage pipeline that can be deployed modularly. It should be noted that while three stages are depicted in FIG. 2, the pipeline architecture can have N stages, where N is a positive integer that is greater than or equal to one and preferably is greater than or equal to two. Unlike the majority of popular machine learning-based studies where tasks are achieved by an end-to-end network architecture, the multi-stage pipeline architecture disclosed herein was adopted due to two major considerations. First, having the independent performance of each stage increases the designer's or user's control over each specific stage by giving them the ability to validate and adjust each stage separately. As a benefit, the pipeline has a strong adaptability, i.e., for new datasets, the trained machine learning system 100 can be transferred by only retraining part of the pipeline with easier-to-obtain labels. Second, the multi-stage pipeline improves the overall interpretability, i.e., with each stage having an explicit purpose, it is possible to determine how each stage is contributing to the final classification decision. Additionally, domain knowledge can be more easily embedded within the pipeline structure.

It should be noted that the inventive principles and concepts are not limited to the multi-stage pipeline architecture shown in FIG. 2, as will be understood by those of skill in the art in view of the discussion provided herein. For example, the inventive principles and concepts disclosed herein can be implemented using a typical end-to-end machine learning architecture, although some of the advantages discussed above may not be realized.

When dealing with databases collected from clinical practice, one of the foremost limitations is the inconsistent image quality. In this embodiment, the quality of fundus images was evaluated in the image quality selector stage 200 using the following criterion: image composition, exposure/contrast, artifacts, and sharpness/focus. Thus, selecting good images out of the whole database is solved by stage 200 as a machine learning image classification task. Specifically, for this embodiment, stage 200 was simulated as a "multi-reviewer" decision-making mechanism by training multiple separate image quality neural network selectors with identical hyper-parameters, structure, and datasets, but with different initialization conditions. For this embodiment, five separate neural network image quality selectors 200*a*-200*e* were used and each retinal fundus image was required to pass all five selectors 200*a*-200*e* unanimously to be included in the Sufficient Image Quality datasets of the Sufficient Image Quality Database 230, which can be stored in memory device 130 or in some other memory device that is accessible by the processor 110. This is a much stricter selection compared with "majority-vote." This strict standard was employed because the inventors anticipated that insufficient images will introduce more potentially non-pathological image features, such as artifacts, which would misguide the final classification and decrease final performance and result interpretability. The UK Biobank originally had 87,567 left fundus images and 88,264 right fundus images. After the image quality selection stage 200 had performed its operations, 21,547 left fundus images and 31,041 right fundus images were extracted into the Sufficient Image Quality Database 230.

Figure 3:
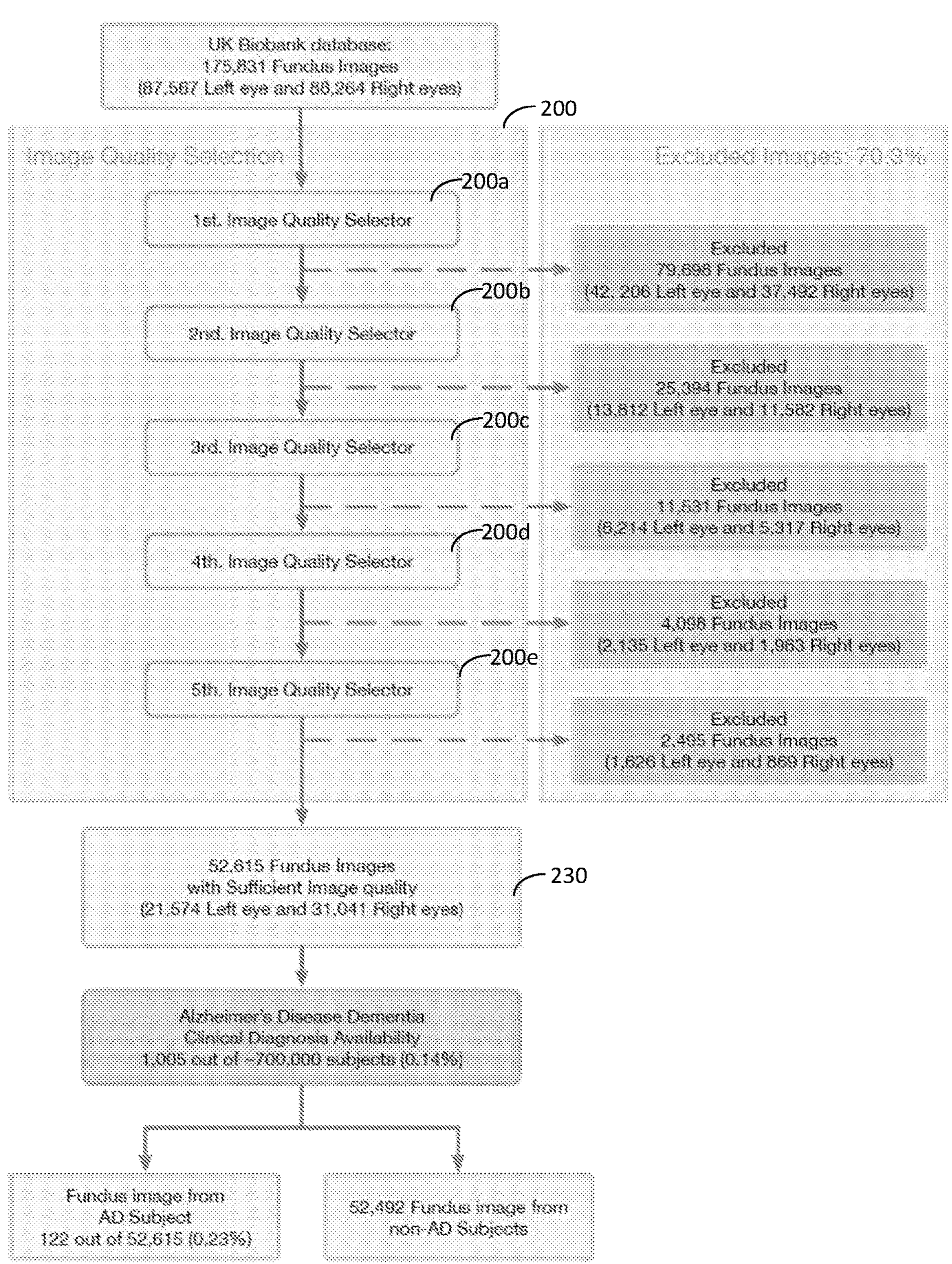
FIG. 3 is a flow diagram illustrating each step of the image quality selection process of the pipeline architecture shown in FIG. 2 in accordance with a representative embodiment.

FIG. 3 is a flow diagram illustrating the selection rate through each step of the image quality selection process in accordance with a representative embodiment. The five selectors 200*a*-200*e* are cascaded, meaning one image is considered to be a Sufficient Quality Image only if it passes all five selectors 200*a*-200*e*. In accordance with this embodiment, each selector 200*a*-200*e* has been trained to make selections based on the criterion listed above, namely, image composition, exposure/contrast, artifacts, and sharpness/focus. The training of each selector 200*a*-200*e* involved inputting fundus images from the database that met and that did not meet all of these criterion until the selectors 200*a*-200*e* were sufficiently trained to identify images of Sufficient Quality and of Insufficient Quality.

Figure 4:
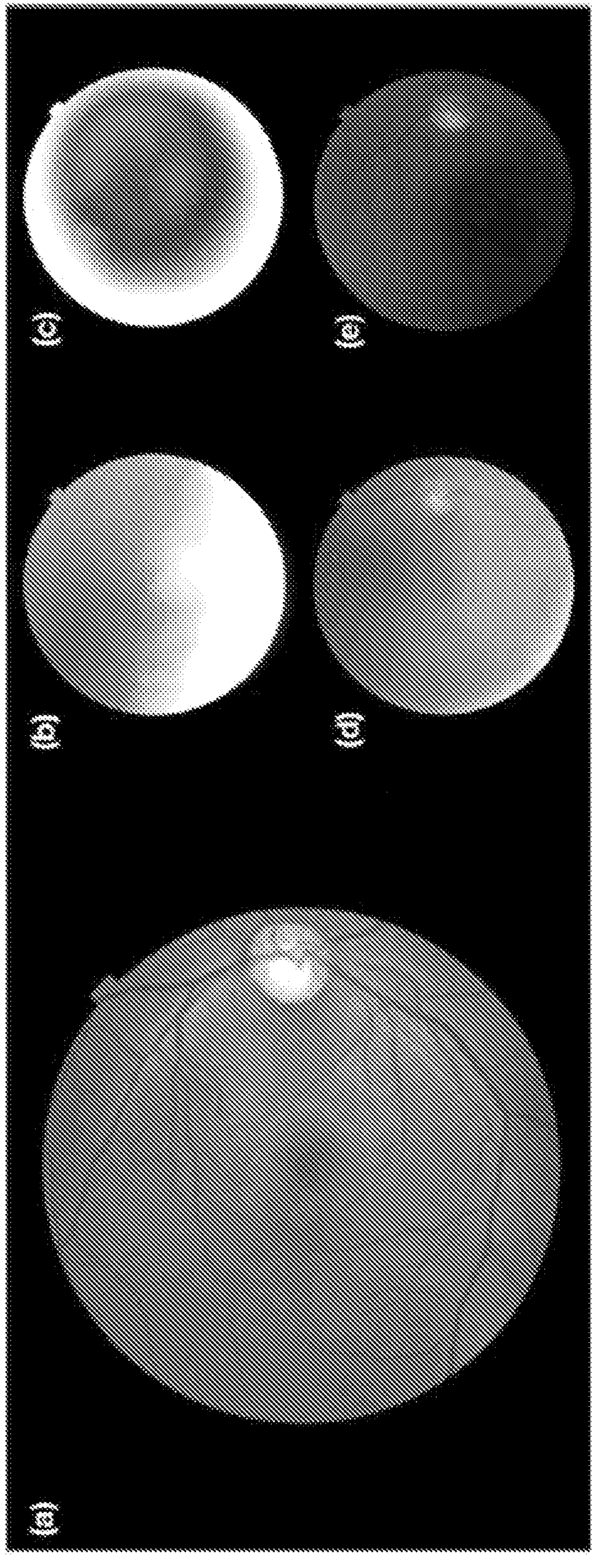
FIG. 4 shows a few examples of fundus images classified by the image quality selection process shown in FIG. 3 as being of sufficient or insufficient image quality in accordance with a representative embodiment.

FIG. 4 shows a few examples of images classified as Sufficient and Insufficient fundus image quality by this quality selection process. Image (a) is a fundus image of ideal image quality. Image (b) is a fundus image of insufficient image quality due to artifacts. Image (c) is a fundus image of insufficient image quality due to bad composition. Image (d) is a fundus image of insufficient image quality due to being out-of-focus. Image (e) is a fundus image of insufficient image quality due to unbalanced and insufficient illumination. After the fundus image quality control, 122 sufficient fundus images from 87 Alzheimer's disease patients were found to have valid Alzheimer's disease dementia labels. Among these 87 Alzheimer's disease patients, 46 are male. The mean age of these Alzheimer's disease subjects is 65.17, with a standard deviation as 4.157. Table 1 shown in FIG. 5 lists the cohort characteristics of all of the extracted groups.

Figures 6A, 6B:
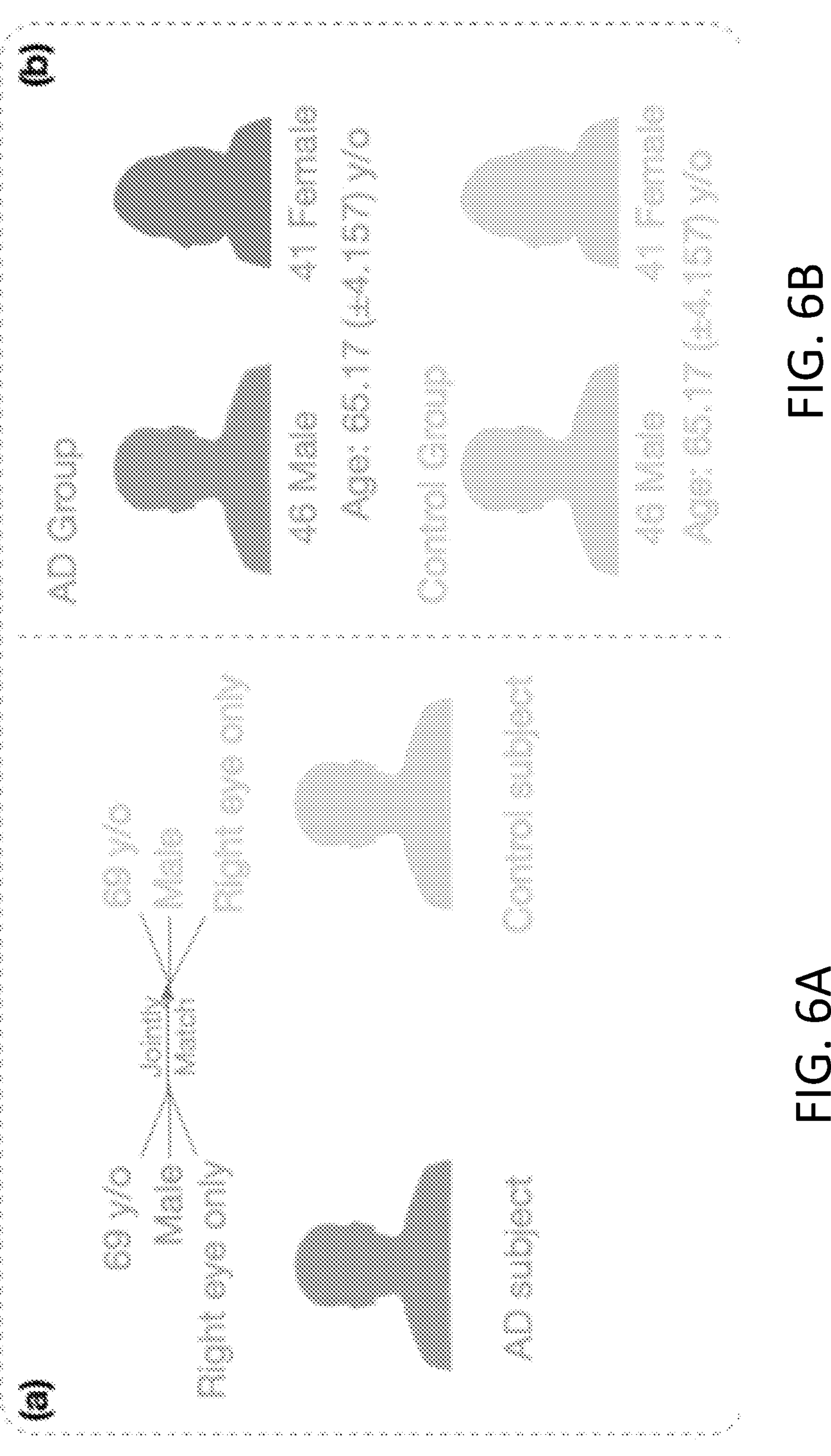
FIGS. 6A and 6B depict the manner in which the AD group subjects and the healthy control group subjects were matched at an individual level in accordance with a representative embodiment.

FIGS. 6A and 6B depict the manner in which control subjects were matched at the individual level in accordance with a representative embodiment. FIG. 6A shows that for each Alzheimer's disease (AD) subject, the matched healthy control subject was selected with the identical combination of gender and age. FIG. 6B shows that, as a result of selecting the control subjects in this manner, the control group and the AD group have identical distributions of gender and age. The matching of healthy control subjects was achieved at an individual-subject level, where for each subject in the Alzheimer's disease group, the healthy counterpart was found by matching both of gender and age (when fundus images were taken). For images that were obtained from the same subject with Alzheimer's Disease, their counterparts were extracted from the same subject as well. This matching standard was used so that the subject-dependent bias will be eliminated as much as possible. As a result, two datasets that were highly controlled for demographical information were obtained, as shown in FIGS. 6A and 6B, for both Alzheimer's disease group and healthy control groups.

The experiments disclosed herein redundantly extracted five control groups for Alzheimer's disease dementia group to evaluate our pipeline's performance. For every subject in the AD group, five different control subjects with the same age, gender, and image for the same eye side as the AD subject were extracted, following the same subject matching procedure. These five subjects were then randomly assigned into five control groups separately.

With reference again to FIG. 2, the pipeline architecture shown proved to be effective at distinguishing Alzheimer's disease from healthy control images. The binary classification performance of the system 100 (FIG. 1) in terms of sensitivity, specificity, classification accuracy, and F-1 score was evaluated. To maximally leverage the current database 230, a nested five-fold cross-validation strategy was employed. Table 2 shown in FIG. 7 lists the performance comparison of the AD group vs. the normal controls (NC) group without feature selection. In Table 2, the mean and standard deviation values were extracted from five-fold cross validations; bold font represents the most optimal performance for each measurement among the five-fold cross validations; italic font represents the least optimal performance; the abbreviations mean the following: AD=dementia caused by Alzheimer's disease, NC=normal control, PPV=positive predictive value, NPV=negative predictive value, TNR=true negative rate, TPR=true positive rate.

Overall, the pipeline architecture achieved a 73.4% binary classification accuracy. Especially, the inventors recognized that the precision of Alzheimer's disease class (77.8%) was much higher than that of the healthy control class (69.4%), while the healthy control class has a higher specificity than Alzheimer's disease group. Also, a receiver operative characteristic curve was used to evaluate the classification performance. The pipeline architecture achieves an area under curve (AUC) as 0.70 and standard deviation as 0.07. Thus, the effectiveness of the pipeline architecture has been demonstrated and proven. The performance is consistent as well based on the small variance measured from the five-fold cross-validation.

To further boost the performance of the system 100, a T-test (p-value=0.01) was employed to select the pixels that carry the most information to distinguish between two groups. With this feature selection, the performance classification accuracy was improved from 68.2% to 82.4%. Table 3 shown in FIG. 8 reports the detailed performance with t-test feature selection. Overall, the result is highly consistent across all healthy control groups, indicating the reported performance does not rely on any specific healthy control group. This demonstrates the effectiveness of the pipeline shown in FIG. 2 has been demonstrated and proven. The performance is consistent as well based on the small variance measured from five-fold cross-validation.

In addition, the effectiveness of the pipeline is not data reliant, as validated by blind-test experiments. Small databases are often viewed as a weakness in machine learning-based studies. One major reason is small databases can easily limit the generality of the trained machine model since a small database is less likely to include all the variance and miss relatively rare datapoints. In addition, the trained machine model can become more data reliant if trained on a smaller database. Data-reliance refers to a situation where the machine learning model overfits the training dataset, and the classification was not actually made based on the general image features, but rather on memorizing the data or co-existent features. One good example is disease classification from medical images collected from multiple sites, where each site uses different scanners with distinct image formats. When certain study sites have a strong association with a specific disease, a high classifications accuracy can be achieved by distinguishing image format on the data collection site, instead of pathological features.

In the study presented herein drawing on a database with over 500,000 individuals, even though the database 230 was limited in terms of the number of fundus images for Alzheimer's disease patients, a much wider choice of healthy control subjects is available. To remedy this small-database drawback, the inventors designed two more sets of experiments as blind-test experiments. First, the inventors defined multiple healthy control groups to repeat the Alzheimer's disease vs. healthy control classification. By repeating the Alzheimer's disease group vs. multiple healthy control groups, the inventors were able to test whether the classification performance was influenced by one specific healthy control group. Second, the classifier stage 220 was trained on two healthy control groups and an attempt was made to classify them from each other as a blind test. If the classifier stage 220 was making classification solely based on the feature difference found between Alzheimer's disease subjects and healthy controls, then this classifier stage 220 is expected to be incapable of distinguishing different healthy control groups. The result of this experiment aligned with the inventors' assumption with an accuracy around 50%, indicating that previously reported classification performance was indeed achieved based on the biomarker specifically associated with Alzheimer's disease group.

Figure 9:
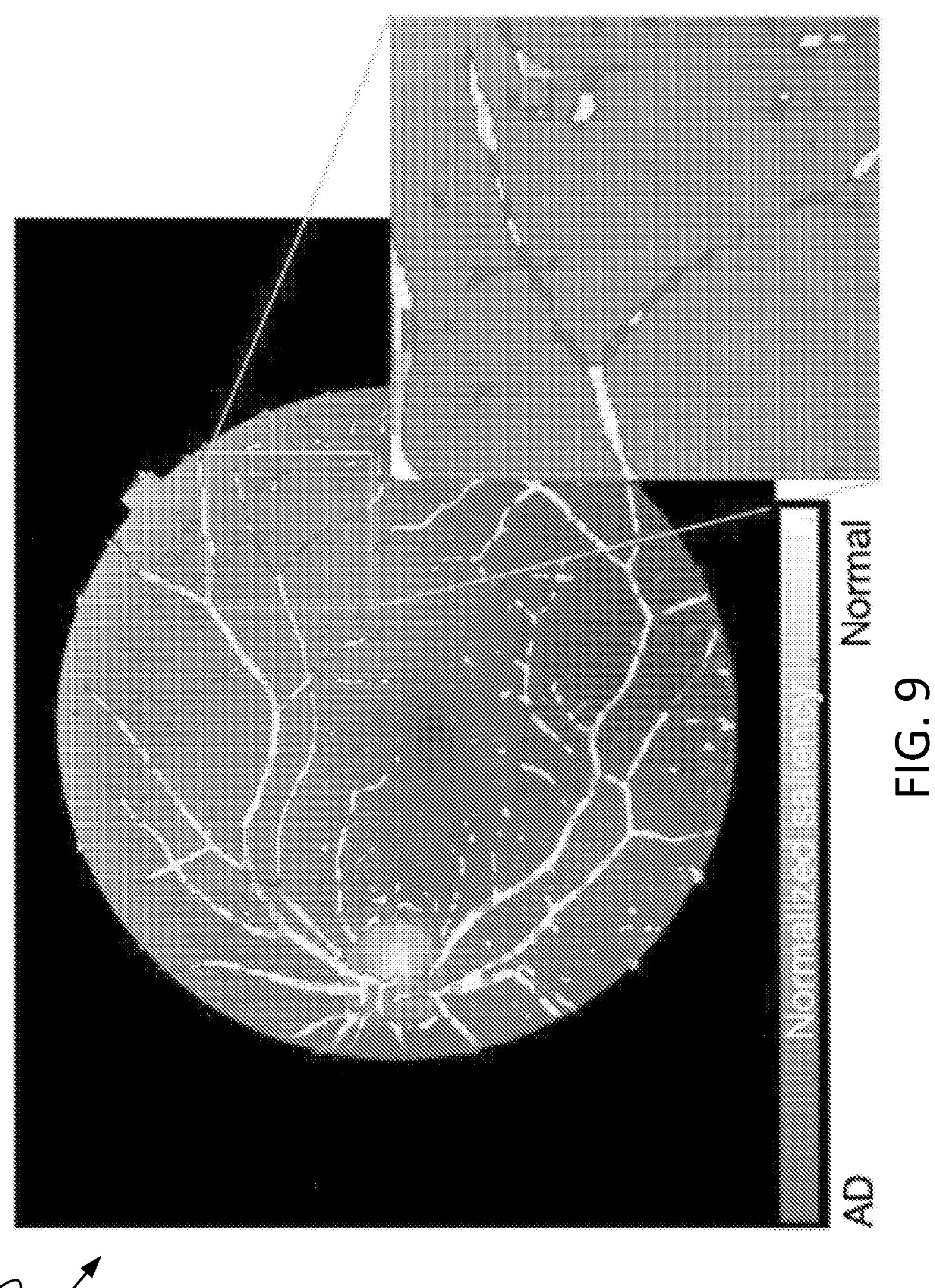
FIG. 9 shows an image of a generated saliency map for an image belonging to an Alzheimer's disease subject generated by the saliency map generator shown in FIG. 2 in accordance with a representative embodiment.

With reference again to FIG. 2, in accordance with this representative embodiment, the classifier stage 220 includes a saliency map generator 240 for generating saliency maps 241. The saliency map 241 shows interpretable features from the trained machine learning model of the classifier stage 220. The saliency map 241 can serve as a biomarker and can be displayed on display device 111 (FIG. 1) and/or printed by the printer 112 (FIG. 1). FIG. 9 shows an image of a generated saliency map 241 generated by the saliency map generator 240 for an image belonging to an AD subject. Darker (e.g., green) pixels are more salient for classifying AD, while lighter (e.g., yellow) pixels do not significantly contribute to this classification result. According to this saliency map, small vessels and capillary vessels are more important in determining whether this image belongs to an AD subject.

This saliency map reflects the importance of different regions from the vessel maps at various levels, from pixel level to a larger 32-by-32 patch area. A general observation that can be made through these saliency maps is that small vessels contribute more than major vessels for the Alzheimer's disease classifier stage 220. The inventors found that this observation aligns with previous studies regarding the vessel map features in Alzheimer's progression. During the process of vessel diameter narrowing and venular degeneration associated with Alzheimer's disease, small vessels are more vulnerable and easier to have morphological changes. Therefore, it is understandable that the trained machine gives higher attention to small vessel areas. Meanwhile, the inventors also observed that even within a small neighborhood, the importance varies greatly on individual pixels. This is a benefit of a machine learning approach because the network can comprehend data at multiple levels, including pixel level, which humans cannot achieve.

Emerging evidence suggests that Alzheimer's disease has a pre-symptomatic period that can be 40-50 years long, since PSEN1 E280A mutation carriers are showing cerebral spinal fluid abnormality as early as in their 20s. Such a long pre-symptomatic period urges us to find a potential in vivo image biomarker that is suitable for timely routine screening of Alzheimer's disease. The present disclosure and the experiments discussed herein focuses on exploring the feasibility to discover potential links between the retina vasculature and Alzheimer's disease using machine learning techniques. With the results disclosed herein from the present experiments, the retina seems to be a strong and effective candidate site for potential biomarker of Alzheimer's disease. There are previous works that attempt to uncover the connection between Alzheimer's disease and the retina. Although highly innovative and inspiring, these previous researches have two major limitations. First, they require intense manual measurement of biomarkers. Second, conventional "group-level" retinal image data analysis techniques are only able to identify average between-group differences and unable to make predictions on individual subjects. This inability to make predictions on the individual level greatly hampered the ability to translate imaging research into clinical practice.

Combined with machine learning techniques, the system and method disclosed herein overcome both of these limitations. First, the machine learning pipeline architecture shown in FIG. 2 is capable of achieving multiple stages of tasks, such as image quality control, vessel map generation, and final classification, in a highly automated fashion. Besides the reduction of manual labor, having a highly automated classification model also helps to eliminate potential human error and bias. Second, this proposed machine learning-based model can bring out a clear classification result, along with an interpretable saliency map that explains which areas of the vessel maps were given special consideration when making a classification decision.

As indicated above, an additional benefit of the system and method is the generality. The inventors trained the model separately for each task stage, utilizing more than one data source. For machine learning techniques, when the developmental datasets and testing datasets are collected from different sources, the domain barrier existent between the two data sources will generally decrease the overall performance and limit the model's generalizability. However, in this study, it was demonstrated that even though different databases were used in the development stage and the validation stage, the overall pipeline still classifies Alzheimer's disease from healthy controls, indicating that the pipeline design overcomes the database domain barrier and achieves higher generality.

The human interpretable biomarker features can be expressed in the form of the saliency map 241. One general observation that can be made from these saliency maps 241 is that the monograph of the venular vessel is critical in making the classification decision, in comparison to major vessels. This observation strongly aligns with other findings. The cerebral vascular contributes to Alzheimer's disease and cognitive impairment. Furthermore, the accumulation of toxic amyloid-beta in the vessel has been suspected to cause dysfunction in blood-brain barrier in aged subject. In addition to cognitive impairment, 84% patients with Alzheimer's disease have also been reported to show morphological substrates of cerebrovascular diseases. Venular degeneration was found to closely associated with Alzheimer's disease in a transgenic animal study. Moreover, retinal venular vessels have been found to be related to multiple diseases such as diabetes, aging, and especially neurodegenerative diseases. On the other hand, machine learning methods are also capable of finding deeper level features. In the present study, it was observed that even in a very small neighborhood on the major vessels, changes associated with individual pixels can be important in making the overall classification conclusion. The machine learning-based technique disclosed herein is capable of making the final decision by considering all pixels. Compared with human experts, such a unique property of the machine learning-based method sheds light on finding retinal imaging biomarkers at a deeper level.

Image Quality Selection

One major challenge in conducting data-driven research with a large-scale non-disease specific database is to deal with data inconsistency introduced by the data collection protocols. Specifically, the fundus images in the UK Biobank have a substantial image quality variability, since fundus images are collected as the viewfinder for OCT images, instead of being a primary data field for diagnosis. Prior to building the machine learning model for Alzheimer's disease vs. healthy controls classification, it is important to have consistently high-quality fundus images for training and testing the classifier 220. Otherwise, the classification results could be negatively impacted by the low image quality. Image quality could be influenced by many other factors than Alzheimer's disease, such as age, scanning site, OCT/fundus scanning protocols. Without controlling the image quality, the classifier 220 could mistakenly classify the disease based on the quality differences. For example, studies show that elderly patients tend to have lower quality fundus images due to the low transparency of their lens.

In accordance with the representative embodiment shown in FIG. 2, the image quality selector 200 is a multi-phase convolutional neural network (CNN)-based image classification network. The factors leading to poor image quality are over- or under-exposure, out of focus, faulty composition, and artifacts. Images with any of the above issues are classified as having "insufficient quality." Similar criteria have been previously used for assessing fundus image quality with machine learning techniques. Following this rating standard, the inventors established a medium-size database 230 with 150 images with sufficient quality and 150 images with insufficient quality to train five independent networks **200*a*-200*e* with the same structure and hyper-parameter, but different random initialization. For each image, the five networks 200*a*-200*e*** return independent classification labels. The image will then be classified as with sufficient quality only if all five independent classifier results agree to be sufficient.

Noteworthily, the definition of sufficient image quality is a subjective topic. Standards vary dependent on clinical demands. In the present study, a relatively stringent standard in image quality selection was applied due to the following machine learning module 220 used for Alzheimer's disease classification. Low quality images input into the machine learning pipeline could generate unexplainable results at the end of the process. The image quality selector 200 ensures that only images with sufficient quality will be used.

Vessel Map Generation

Segmenting vessel maps from fundus images is a typical image segmentation task and can be confidently achieved by using U-net as the CNN-based vessel map generator 210, although other map generators may be used for this purpose. The inventive principles and concepts are not limited to using any particular type of vessel map generator for this purpose. During the development process, the vessel map generator 210, which is a vessel segmentation deep learning model in this representative embodiment, was trained on the Digital retinal Images For Vessel Extraction (DRIVE) database and evaluated on the UK Biobank dataset. Indeed, it is a less common practice in developing a machine learning-based model to train on one database and apply it to a different database. The reason for doing so for this embodiment is based on one important reason, namely, to test the generality of the method of the present disclosure. When the trained model is presented to a new database, it can be expected that this trained model may not work well without proper domain adaptation. However, in the clinical setting, it is almost unavoidable that data are collected from different sites using different devices, introducing device-based domain variation into the database. Current development/validation dataset configuration enabled the inventors to determine the robustness of the pipeline architecture when facing an unseen database.

Alzheimer's Disease Classification in accordance with this representative embodiment, the Alzheimer's disease classifier model 220 is a binary support vector machine (SVM)-based classifier, although other types of classifiers may be used for this purpose. The input to the SVM is vectorized vessel maps 211 (e.g., $280^2$-by-1), and the output is a binary scalar, representing if the fundus image came from a subject with Alzheimer's disease or heathy control. Based on empirical results, a Gaussian radial basis function (RBF) was chosen as the SVM kernel. As indicated above, a nested five-fold cross-validation protocol was applied for developing and testing the overall classification performance based on the whole 122 vessel map images. Cross-validation protocols are very commonly used techniques for training/developing deep learning-based pipelines. Persons of skill in the art will understand the manner in which a suitable cross-validation protocol can be implemented. Therefore, in the interest of brevity, a detailed discussion of the manner in which the protocol is implemented will not be provided herein. Basically, the entire dataset was divided into five folds, with four external folds for training and validation, and one external fold left for testing in each round. Inside the training and validation data, another internal five-fold cross-validation is performed to optimize hyper-parameters in the RBF SVM using a grid search. The optimal hyper-parameters were used to train an SVM model 220 that was tested on the one external fold left out. This process is done five times, so each external fold was used as test data once. The overall performance was reported as the average performance on all folds. RBF SVM is a very widely used technique as well, and therefore will not be described herein in further detail.

Attention Maps

Figure 10:
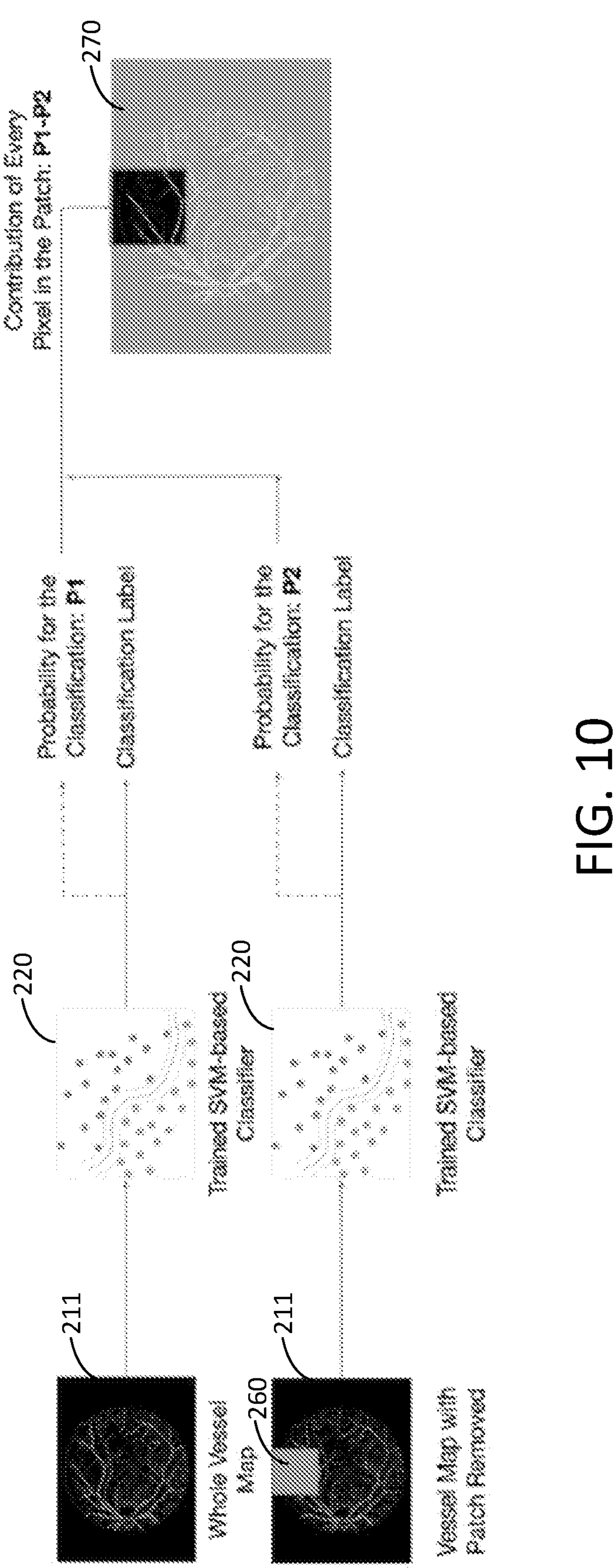
FIG. 10 is a flow diagram illustrating the generation of attention maps that generated for verification purposes.

FIG. 10 is a flow diagram illustrating the generation of attention maps that were generated for verification purposes. Machine learning-based techniques generally have a limitation in lack of interpretability. In order to increase the interpretability, the inventors obtained attention maps by performing occlusion tests on the vessel maps 211 to visualize the contribution of different parts of the vascular system to the machine learning prediction. In addition to the blind tests discussed above, the inventors used another approach to verify if the trained machined learning model was capturing image features of anatomical or pathological indications. Specifically, the inventors defined a set of patches 260 with various sizes, ranging from 1-by-1 (pixel), 2-by-2, 4-by-4, to 8-by-8. Then, for each patch size, the patch 260 was moved in a sliding window fashion over the entire vessel map 211, setting the pixels overlapping with the patch to zero (black out) and calculating the importance of regions covered by the patch 260 as the change in prediction confidence for the output label 270. Eventually, importance scores at each pixel location across all patch scales were summarized and normalized to generate attention maps, where the intensity of each pixel represents its importance.

Treatment

Once trained, the machine learning system 100 can be employed in a clinical setting to predict Alzheimer's disease, which can then be treated in a clinical setting. Since it is relatively easy to use the system 100 for routine screening of patients for Alzheimer's disease, the system 100 can be used as part of a treatment process to monitor the treatment process and select the optimal treatment strategy based on the prediction made by the classifier model 220. Once the classifier model 220 has been trained, the role of the image quality selection model 200 ends. During the treatment process, the fundus image obtained from the patient is processed by the vessel map model 210 to obtain the vessel map 211, which is then processed by the classifier model 220 to obtain the Alzheimer's disease prediction. Treatment can then be optimized based on the prediction.

Figure 11:
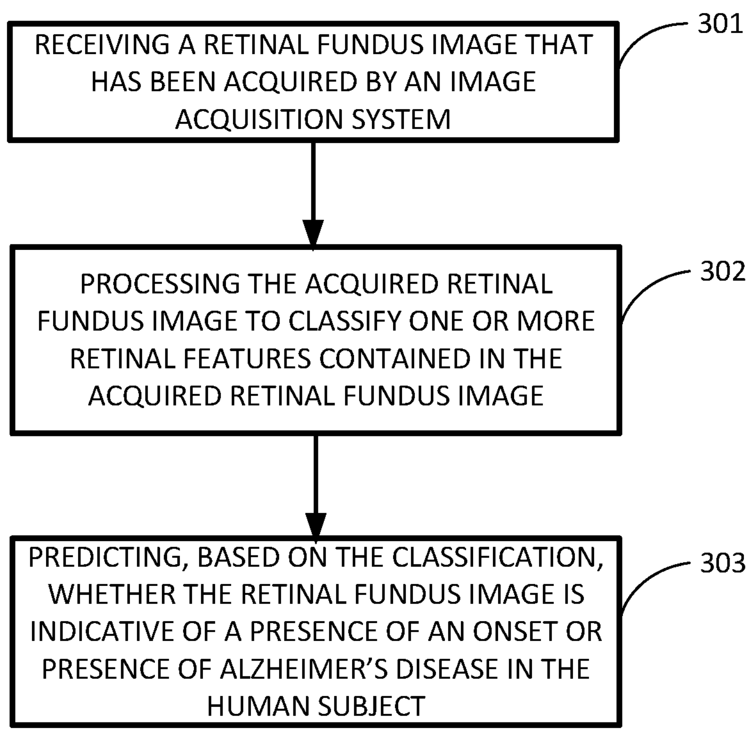
FIG. 11 is a flow diagram representing the machine learning method in accordance with a representative embodiment for classifying retinal features and for predicting, based on the classified retinal features, an onset or presence of Alzheimer's disease in a human subject.

FIG. 11 is a flow diagram representing the machine learning method in accordance with a representative embodiment for classifying retinal features and for predicting, based on the classified retinal features, an onset or presence of Alzheimer's disease in a human subject. Block 301 represents the processor that performs the trained machine learning model receiving a retinal fundus image that has been acquired by an image acquisition system. Block 302 represents the processor that performs the trained machine learning model processing the acquired retinal fundus image to classify one or more retinal features contained in the acquired retinal fundus image. Block 303 represents the processor that performs the trained machine learning model predicting, based on the classification, whether the retinal fundus image is indicative of an onset or presence of Alzheimer's disease in the human subject.

It should be noted that any or all portions of the algorithms described above that are implemented in software and/or firmware being executed by a processor (e.g., processor 110) can be stored in a non-transitory memory device, such as the memory 130. For any component discussed herein that is implemented in the form of software, any one of a number of programming languages may be employed such as, for example, C, C++, C #, Objective C, Java®, JavaScript®, Perl, PHP, Visual Basic®, Python®, Ruby, Flash®, or other programming languages. The term "executable" means a program file that is in a form that can ultimately be run by the processor 110. Examples of executable programs may be, for example, a compiled program that can be translated into machine code in a format that can be loaded into a random access portion of the memory 130 and run by the processor 110, source code that may be expressed in proper format such as object code that is capable of being loaded into a random access portion of the memory 130 and executed by the processor 110, or source code that may be interpreted by another executable program to generate instructions in a random access portion of the memory device 130 to be executed by the processor 110, etc. An executable program may be stored in any portion or component of the memory 130 including, for example, random access memory (RAM), read-only memory (ROM), hard drive, solid-state drive, USB flash drive, memory card, optical disc such as compact disc (CD) or digital versatile disc (DVD), floppy disk, magnetic tape, static random access memory (SRAM), dynamic random access memory (DRAM), magnetic random access memory (MRAM), a programmable read-only memory (PROM), an erasable programmable read-only memory (EPROM), an electrically erasable programmable read-only memory (EEPROM), or other like memory device.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. A machine learning system that classifies retinal features and predicts, based on the classified retinal features, an onset or presence of Alzheimer's disease in a human subject, the system comprising:

a processor configured to perform at least one trained machine learning model configured in a multiple-stage (multi-stage) pipeline architecture comprising at least first, second, and third stages in series, the second stage following the first stage and the third stage following the second stage, the first, second, and third stages comprising, respectively, a trained image quality selector machine learning model, a trained vessel map generator machine learning model and a trained Alzheimer disease classifier machine learning model, wherein each of the at least first, second, and third stages are separately trained, said at least one trained machine learning model has been trained on stored retinal fundus images obtained from at least a first group of human subjects who have previously been diagnosed as having Alzheimer's disease and at least a first group of human subjects who have not previously been diagnosed as having Alzheimer's disease, said at least one trained machine learning model performing a process comprising:

receiving a retinal fundus image that has been acquired by an image acquisition system in a clinical setting;

processing the acquired retinal fundus image at a pixel level to classify one or more retinal features contained in the acquired retinal fundus image, where the trained vessel map generator machine learning model generates a respective vessel map from the retinal fundus image via vessel segmentation; and predicting, based on the classification, whether the retinal fundus image is indicative of an onset or presence of Alzheimer's disease in the human subject, where the trained Alzheimer disease classifier machine learning model processes the respective vessel map to predict whether the retinal fundus image is indicative of the onset or presence of Alzheimer's disease, and where a treatment strategy is selected based on the prediction and communicated for implementation in the clinical setting and treatment of the human subject is initiated based upon the treatment strategy; and a memory device in communication with the processor.

2. The machine learning system of claim 1, wherein said at least one trained machine learning model is implemented in computer instructions stored in the memory device for execution by the processor.

3. The machine learning system of claim 1, wherein the trained image quality selector machine learning model is used during training of the Alzheimer disease classifier machine learning model to classify retinal fundus images inputted to the first stage as being either of sufficient image quality or insufficient image quality based upon image composition, exposure/contrast, artifacts, and sharpness/focus and to output retinal fundus images classified as being of sufficient image quality to the second stage, and wherein during training of the Alzheimer disease classifier machine learning model, the trained vessel map generator machine learning model generates respective vessel maps for each respective retinal fundus image inputted to the second stage and outputs the vessel maps to the third stage, and wherein during training of the Alzheimer disease classifier machine learning model, the vessel maps outputted to the third stage are used to train the Alzheimer's disease classifier model.

4. The machine learning system of claim 1, wherein after the Alzheimer disease classifier machine learning model has been trained to classify retinal fundus images as being from a human subject having Alzheimer's disease, a retinal fundus image obtained from a patient is processed by the trained vessel map generator machine learning model to produce the respective vessel map that is outputted to the third stage, and wherein the respective vessel map is processed by the trained Alzheimer disease classifier machine learning model to predict, based on the classification, whether the retinal fundus image is indicative of an onset or presence of Alzheimer's disease in the human subject.

5. The machine learning system of claim 4, further comprising a saliency map generator in the third stage for generating respective saliency maps from respective vessel maps generated by the trained vessel map generator learning machine model, where the saliency maps indicate vessel map pixels that are salient to classification to Alzheimer's disease and vessel map pixels that do not significantly contribute to the classification of Alzheimer's disease.

6. The machine learning system of claim 1, wherein the trained image quality selector machine learning model comprises multiple trained image quality selector machine learning models arranged in a pipeline, and wherein a retinal fundus image is only outputted to the second stage if all of the trained image quality selector machine learning models classified the retinal fundus image as being of sufficient image quality.

7. A machine learning method for classifying retinal features and for predicting, based on the classified retinal features, an onset or presence of Alzheimer's disease in a human subject, the method comprising:

in a processor configured to perform at least one trained machine learning model configured in a multiple-stage (multi-stage) pipeline architecture comprising at least first, second, and third stages in series, the second stage following the first stage and the third stage following the second stage, the first, second, and third stages comprising, respectively, a trained image quality selector machine learning model, a trained vessel map generator machine learning model and a trained Alzheimer disease classifier machine learning model:

receiving a retinal fundus image that has been acquired by an image acquisition system in a clinical setting;

processing the acquired retinal fundus image at a pixel level to classify one or more retinal features contained in the acquired retinal fundus image, where the trained vessel map generator machine learning model generates a respective vessel map from the retinal fundus image via vessel segmentation; and predicting, based on the classification, whether the retinal fundus image is indicative of an onset or presence of Alzheimer's disease in the human subject, where the trained Alzheimer disease classifier machine learning model processes the respective vessel map to predict whether the retinal fundus image is indicative of the onset or presence of Alzheimer's disease, and where a treatment strategy is selected based on the prediction and communicated for implementation in the clinical setting and treatment of the human subject is initiated based upon the treatment strategy; and wherein each of the at least first, second, and third stages are separately trained, said at least one trained machine learning model has been trained on stored retinal fundus images obtained from at least a first group of human subjects who have previously been diagnosed as having Alzheimer's disease and at least a first group of human subjects who have not previously been diagnosed as having Alzheimer's disease.

8. The machine learning method of claim 7, wherein the trained image quality selector machine learning model is used during training of the Alzheimer disease classifier machine learning model to classify retinal fundus images inputted to the first stage as being either of sufficient image quality or insufficient image quality based upon image composition, exposure/contrast, artifacts, and sharpness/focus and outputting retinal fundus images classified as being of sufficient image quality to the second stage, and wherein during training of the Alzheimer disease classifier machine learning model, the trained vessel map generator machine learning model generates respective vessel maps for each respective retinal fundus image inputted to the second stage and outputs the vessel maps to the third stage, and wherein during training of the Alzheimer disease classifier machine learning model, the vessel maps outputted to the third stage are used to train the Alzheimer's disease classifier model.

9. The machine learning method of claim 7, wherein after the Alzheimer disease classifier machine learning model has been trained to classify retinal fundus images as being from a human subject having Alzheimer's disease, a retinal fundus image obtained from a patient is processed during the processing step by the trained vessel map generator machine learning model to produce the respective vessel map that is outputted to the third stage, and wherein the respective vessel map is processed by the trained Alzheimer disease classifier machine learning model during the predicting step to predict, based on the classification, whether the retinal fundus image is indicative of an onset or presence of Alzheimer's disease in the human subject.

10. The machine learning method of claim 7, wherein the trained Alzheimer disease classifier machine learning model further comprises a saliency map generator for generating respective saliency maps from respective vessel maps generated by the trained vessel map generator learning machine model, where the saliency maps indicate vessel map pixels that are salient to classification to Alzheimer's disease and vessel map pixels that do not significantly contribute to the classification of Alzheimer's disease.

11. A non-transitory computer-readable storage medium, comprising a machine learning model comprising computer instructions for execution by a processor of at least one computer system or computing device for classifying retinal features and for predicting, based on the classified retinal features, an onset or presence of Alzheimer's disease in a human subject, the machine learning model comprising:

at least one trained machine learning model, the trained machine learning model configured in a multiple-stage (multi-stage) pipeline architecture comprising at least first, second, and third stages in series, the second stage following the first stage and the third stage following the second stage, the first, second, and third stages comprising, respectively, a trained image quality selector machine learning model, a trained vessel map generator machine learning model and a trained Alzheimer disease classifier machine learning model, where execution of the at least one trained machine learning model causes the at least one computer system or computing device to at least:

receive a retinal fundus image that has been acquired by an image acquisition system in a clinical setting;

process the acquired retinal fundus image at a pixel level to classify one or more retinal features contained in the acquired retinal fundus image, where the trained vessel map generator machine learning model generates a respective vessel map from the retinal fundus image via vessel segmentation; and predict, based on the classification, whether the retinal fundus image is indicative of an onset or presence of Alzheimer's disease in the human subject, where the trained Alzheimer disease classifier machine learning model processes the respective vessel map to predict whether the retinal fundus image is indicative of the onset or presence of Alzheimer's disease, and where a treatment strategy is selected based on the prediction and communicated for implementation in the clinical setting and treatment of the human subject is initiated based upon the treatment strategy; and wherein each of the at least first, second, and third stages are separately trained, said at least one trained machine learning model has been trained on stored retinal fundus images obtained from at least a first group of human subjects who have previously been diagnosed as having Alzheimer's disease and at least a first group of human subjects who have not previously been diagnosed as having Alzheimer's disease.

12. The non-transitory computer-readable storage medium of claim 11, wherein the trained image quality selector machine learning model is used during training of the Alzheimer disease classifier machine learning model to classify retinal fundus images inputted to the first stage as being either of sufficient image quality or insufficient image quality based upon image composition, exposure/contrast, artifacts, and sharpness/focus and outputting retinal fundus images classified as being of sufficient image quality to the second stage, and wherein during training of the Alzheimer disease classifier machine learning model, the trained vessel map generator machine learning model generates respective vessel maps for each respective retinal fundus image inputted to the second stage and outputs the vessel maps to the third stage, and wherein during training of the Alzheimer disease classifier machine learning model, the vessel maps outputted to the third stage are used to train the Alzheimer's disease classifier model.

13. The non-transitory computer-readable storage medium of claim 12, wherein after the Alzheimer disease classifier machine learning model has been trained to classify retinal fundus images as being from a human subject having Alzheimer's disease, a retinal fundus image obtained from a patient is processed by the trained vessel map generator machine learning model to produce the respective vessel map that is outputted to the third stage, and wherein the respective vessel map is processed by the trained Alzheimer disease classifier machine learning model to predict, based on the classification, whether the retinal fundus image is indicative of an onset or presence of Alzheimer's disease in the human subject.

14. The non-transitory computer-readable storage medium of claim 11, wherein the Alzheimer disease classifier machine learning model comprises a saliency map generator in the third stage for generating respective saliency maps from respective vessel maps generated by the trained vessel map generator learning machine model, where the saliency maps indicate vessel map pixels that are salient to classification to Alzheimer's disease and vessel map pixels that do not significantly contribute to the classification of Alzheimer's disease.

* * * * *